United States Patent [19]

Hastings

[11] Patent Number: 5,068,085
[45] Date of Patent: Nov. 26, 1991

[54] INSTRUMENT STERILIZER

[76] Inventor: Joseph A. Hastings, 2124 Dorchester Dr., Mobile, Ala. 36695

[21] Appl. No.: 258,888

[22] Filed: Oct. 17, 1988

[51] Int. Cl.$^5$ ................................................ F28C 3/10
[52] U.S. Cl. .......................................... 422/1; 422/307; 432/215
[58] Field of Search ............................ 422/1, 38, 307; 165/104.15, 104.18; 432/214, 215

[56] References Cited

U.S. PATENT DOCUMENTS

| 1,107,834 | 8/1914 | Perrin | 422/307 |
| 2,127,932 | 8/1938 | Pellkofer | 422/307 |
| 3,983,931 | 10/1976 | Whitehead et al. | 165/104.16 |
| 4,054,376 | 10/1977 | Wareham | 165/104.16 |
| 4,094,633 | 6/1978 | Peterson et al. | 432/215 |
| 4,121,091 | 10/1978 | Wareham | 165/104.16 |

Primary Examiner—Robert J. Warden
Assistant Examiner—Howard Hampel
Attorney, Agent, or Firm—Jennings, Carter, Thompson & Veal

[57] ABSTRACT

A sterilizer for medical or dental instruments utilizes a reservoir of reusable heat transfer beads, a preselected quantity of which are released into an instrument tray containing instruments to be sterilized. The tray and beads are positioned within a heating column for sterilization and the tray with beads is thereafter removed to the top of the column for instant utilization. The beads are released through the bottom of the tray into the reservoir for reheating.

17 Claims, 2 Drawing Sheets

INSTRUMENT STERILIZER

FIELD OF THE INVENTION

The present invention relates to the field of sterilizing or cleansing of small objects such as medical or dental instruments and the like. More particularly the present invention relates to apparatus for iteratively sterilizing instruments using the same heat transfer media in a manner that presents sterilized instruments for use while sterilizing additional instruments.

BACKGROUND OF THE INVENTION

The medical/dental profession has long been conscious of the need for sterilizing their reusable instruments. An early sterilizer for dental or surgical instruments is disclosed in U.S. Pat. No. 648,242. Further advancement of the art is shown in U.S. Pat. No. 1,275,676, and more recently in U.S. Pat. Nos. 4,376,096 to Bowen; 4,448,750 to Fuesting; and 4,541,992 to Jerge et al. While each of these apparatus are satisfactory for their intended purpose it is clear that in the modern office setting wherein the dentist or doctor sees a number of patients in sequence an apparatus is needed which may be iteratively used to present sterilized instruments for use while sterilizing additional instruments.

SUMMARY OF THE INVENTION

It is the object of the present invention to provide a means for iteratively sterilizing small objects using the same heat transfer medium.

Another object of the invention is to provide a sterilization apparatus which presents sterilized instruments, for use while sterilizing additional instruments, at an unprecedented time estimate of under one minute.

To achieve the objects of this invention I employ a reservoir of heat transfer beads, which have good heat retention and conductive characteristics such as those used in U.S. Pat. No. 4,054,376, and a column of heat transfer material. My reservoir is open at the top and has a displaceable partition which allows the heat transfer beads to descend into the column. Beneath the reservoir I provide a second displaceable member thereby defining a fixed volume within the column which volume holds a measured quantity of the heat transfer beads. Spaced beneath the second displaceable member is an instrument tray which can be removed from within the column and placed atop the column above the reservoir. The instrument tray has a bottom which selectively allows heat transfer beads to pass therethrough. Thus when the tray is placed atop the column the beads can be released into the reservoir for reheating and reuse.

BRIEF DESCRIPTION OF THE DRAWINGS

Apparatus embodying features of my invention are depicted in the accompanying drawings which form a portion of this application and wherein.

DESCRIPTION OF A PREFERRED EMBODIMENT

Figure 1:
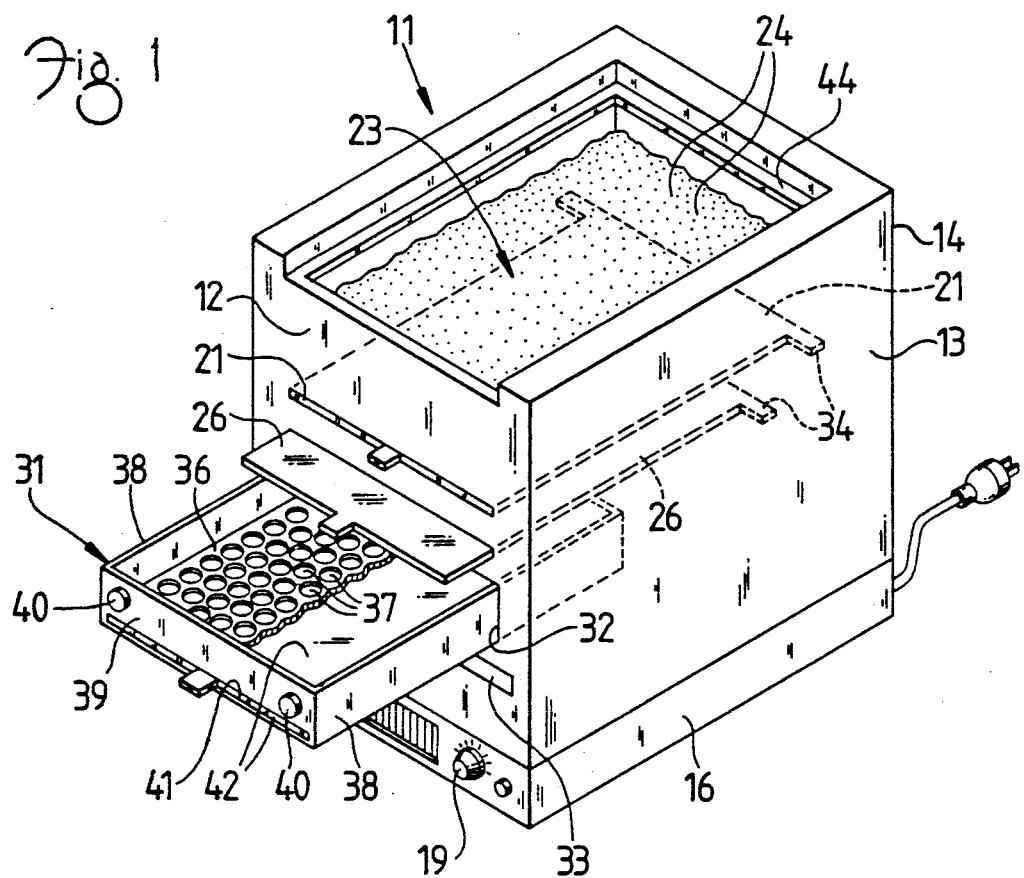
FIG. 1 is a perspective view of the apparatus showing the instrument tray extended.
Figure 2:
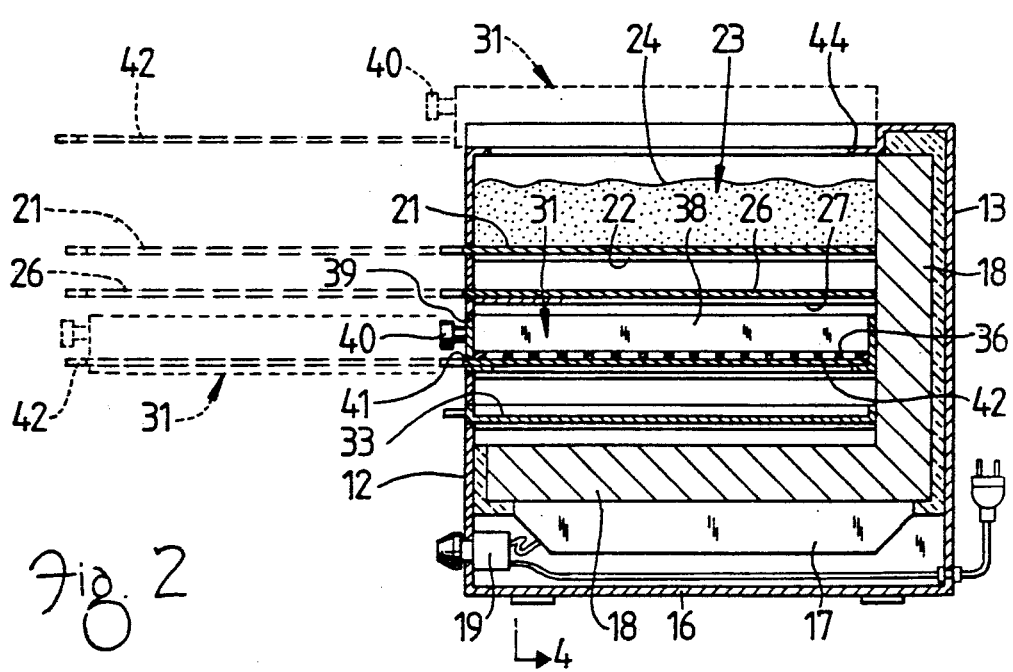
FIG. 2 is a sectional view taken along adjacent one side of the apparatus shown in FIG. 1.
Figure 3:
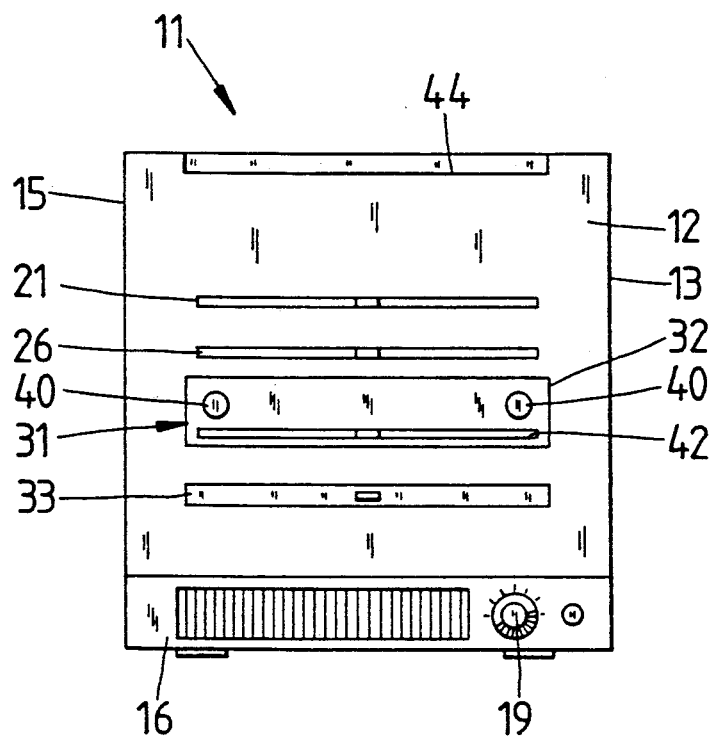
FIG. 3 is a front elevational view of the apparatus.
Figure 4:
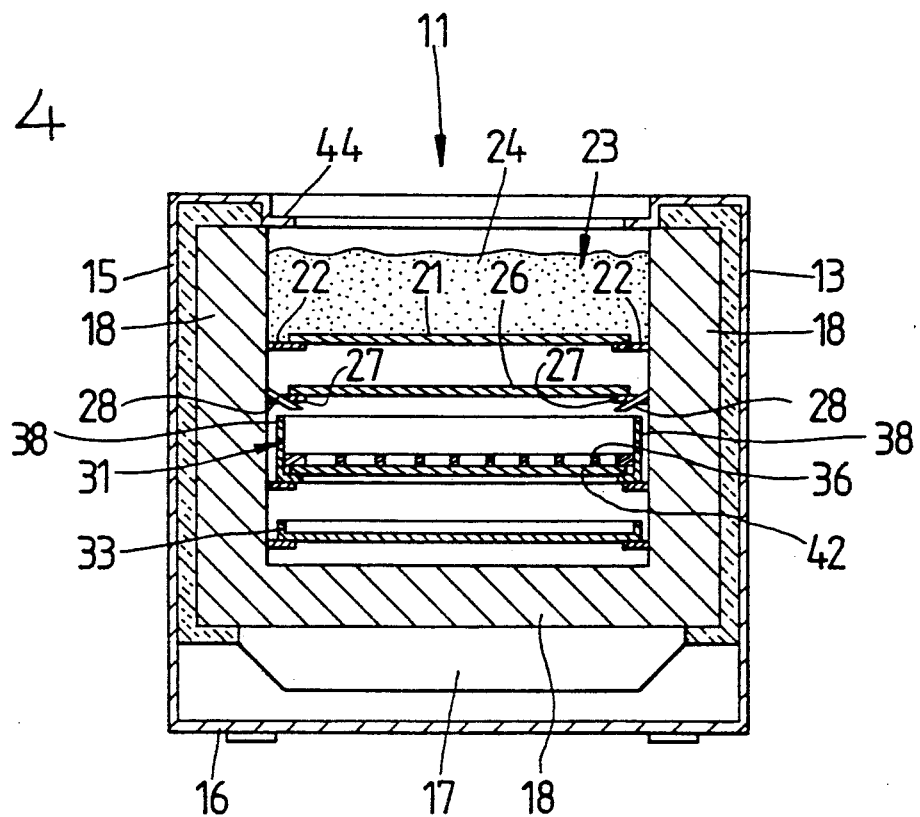
FIG. 4 is a sectional view taken along line 4—4 of FIG. 2.

Referring to the drawings it may be seen in FIG. 1 that my sterilizer shown generally at 11 is essentially an open topped column having upstanding sidewalls 12-15 and a base 16. The base 16 includes a heater element 17 which is in thermal communication with heat transfer materials 18 in each wall 12-15. A rheostat 19 or some other temperature control may also be included in the base 16 to permit variation of the temperature.

The upper portion of the column is separated from the lower portion by a bead control tray 21 which is slidably mounted through wall 12 and rests on a set of inwardly facing flanges 22 extending inwardly from walls 13 and 15. This upper portion serves as a reservoir 23 for a quantity of heat retentive beads 24 which are used as a heat transfer media in this invention. The beads 24 in the reservoir 23 are in thermal communication with the heat transfer material 18 and are thus heated to a temperature sufficient to sterilize the beads 24.

Spaced below the reservoir 23 is a second horizontally extending partition 26 which may be a second bead control tray or a louvered panel biased toward a closed position. The partition 26 is positioned at a predetermined distance from the reservoir to define a particular volume within the column. As with bead control tray 21 the partition 26 may also rest on a set of inwardly extending flanges 27. Extending downwardly and inwardly from proximal the flanges 27 are a set of deflectors 28 which deflect heat transfer beads 24 toward the center of the column, thereby enhancing the probability that the beads 24 will be retained in an instrument tray 31 which is removably inserted into an opening 32 in the column and is supported therein. Also inserted into the wall 12 at a distance beneath the instrument tray 31 is an overflow tray 33.

Note that instrument tray 31 and overflow tray 33 are removable from the column, however bead control tray 21 and partition 26 need not be removable and thus may have a set of tabs 34 or stops to prevent inadvertent removal.

As may be seen in FIG. 1, the instrument tray 31 has a bottom member 36 which includes a plurality of apertures 37 thereon, each aperture 37 being larger in diameter than the individual heat transfer beads 24. The bottom member 36 has attached thereto upstanding sides 38 including a front member 39 which has thereon one or more knobs 40 which may be used to remove the tray 31 from the column. The front member 39 also has a slot 41 extending therethrough just below the junction of the front member 39 and the bottom member 36. The slot 41 has slidably inserted therein a bead control panel 42 which is substantially coextensive with the bottom member 36 and when fully inserted into the slot 41 serves to close all of the apertures 37 in the base member 36, and likewise when fully withdrawn, opens all of the apertures.

The top of the column as heretofore noted is open and has formed thereon a seat 44 on which the instrument tray 31 may be placed.

In operation, a quantity of heat transfer beads 24 are placed in the reservoir 23 above bead control tray 21 and heat from heater 16 is transferred upward thereto such that the beads 24 become sufficiently heated as to serve as a sterilization medium. An instrument tray 31 bearing instruments to be sterilized is inserted into the column at opening 32. With the partition 26 blocking the interior of the column, bead control tray 21 is withdrawn and reinserted, thereby allowing a quantity of heated heat transfer beads 24 to fill the volume defined by the column, the partition 26 and the bead control tray 21. The partition 26 is then removed or opened to allow the hot heat transfer beads to fall into and fill the instrument tray 31 where they give up heat to the contained instruments and raise the temperature of the instruments sufficiently to sterilize the same. Note that the quantity of beads 24 required to effect proper heat transfer determines the volume of the heat transfer tray. Bead temperature is maintained via the heat transfer material 18. Once the instruments reach 360° F. they are sterilized and removed for storage or use. My sterilizer is ready for immediate use to sterilize the next group of instruments.

When the instrument tray 31 is removed from opening 32 it is placed on the seat 44 atop the column. The bead control panel 42 is then withdrawn to permit the heat transfer beads 24 to pass through the bottom member 36 into the column where they are reheated in the reservoir 23. A second instrument tray may be inserted into opening 32 for sterilization of instruments while the first tray is in place on seat 44.

From the foregoing it may be seen that I have devised an instrument sterilization system which is compact and efficient, that permits iterative processing of instruments using a reusable sterilization medium and which enables the practitioner to sterilize one set of instruments while using another.

While I have shown my invention in one form, it will be obvious to those skilled in the art that it is not so limited but is susceptible of various changes and modifications without departing from the spirit thereof.

What I claim is:

1. Apparatus for sterilizing dental instruments and the like comprising:
   (a) a container having an internal cavity and a set of upstanding walls having at least an inner portion of heat transferring material;
   (b) means for providing heat to said walls in a controllable manner;
   (c) a plurality of heat transfer beads;
   (d) an instrument tray including means for selectively retaining or releasing said beads within said tray, said tray adapted for cooperative insertion into said container through an opening in one wall of said container;
   (e) means for retaining a quantity of beads within said container above an instrument tray inserted in said opening; and
   (f) means for releasing a predetermined quantity of beads into said instrument tray from said means for retaining.

2. Apparatus as defined in claim 1 wherein said instrument tray comprises:
   (a) a perforated bottom member having perforations of a size which permit the passage of said beads through said bottom member;
   (b) a plurality of upstanding side members affixed to said bottom member along the periphery thereof and joined to each other forming a defined volume above said bottom member; and
   (c) a bead control panel coplanar and substantially coextensive with said bottom member, said bead control panel removably inserted adjacent said bottom member through a slot formed in one of said sidewalls.

3. Apparatus as defined in claim 2 wherein means for retaining a quantity of beads comprises a first bead control tray removably insertable into said cavity through said one wall at a preselected height, said tray being generally coextensive with the internal cross-section of said cavity.

4. Apparatus as defined in claim 3 wherein said means for releasing a predetermined quantity of beads comprises a second bead control tray insertable into said cavity through said one wall at a predetermined distance below said first bead control tray such that a fixed volume is defined between said trays.

5. Apparatus as defined in claim 4 further comprising a plurality of flange members extending within said cavity for supporting said first and second bead control trays and said instrument tray thereon and a bead deflector flange extending downwardly and inwardly within said cavity above the height of said opening for said instrument tray.

6. Apparatus as defined in claim 1 wherein means for retaining a quantity of beads comprises a first bead control tray removably insertable into said cavity through said one wall at a preselected height, said tray being generally coextensive with the internal cross-section of said cavity.

7. Apparatus as defined in claim 6 wherein said means for releasing a predetermined quantity of beads comprises a second bead control tray insertable into said cavity through said one wall at a predetermined distance below said first bead control tray such that a fixed volume is defined between said trays.

8. Apparatus as defined in claim 1 wherein said container is open at the top and includes a seat for receiving said instrument tray thereon.

9. The apparatus as defined in claim 1 further comprising means for insulating the exterior of said container.

10. A method for sterilizing dental instruments and the like comprising the steps of:
    (a) heating a quantity of heat transfer beads within a reservoir therefor in a heated cavity;
    (b) placing an instrument tray containing instruments in said cavity beneath said reservoir;
    (c) releasing a predetermined quantity of said heat transfer beads into said instrument tray such that heat is transferred to instruments therein;
    (d) removing said instrument tray from said cavity after a predetermined time;
    (e) positioning said instrument tray above said reservoir and cavity; and
    (f) returning said heat transfer beads from said instrument tray into said cavity for reheating in said reservoir while retaining said instruments in the tray.

11. The method as defined in claim 10 wherein said releasing step comprises:
    (a) forming a retention chamber having a predetermined volume beneath said reservoir;
    (b) releasing a quantity of heat transfer beads into said predetermined volume; and
    (c) releasing the heat transfer beads within said predetermined volume onto said tray.

12. Apparatus for sterilizing dental instruments and the like comprising:
    (a) a tray for holding instruments;

(b) means for heating a plurality of heat transfer beads within a reservoir;

(c) means for dispensing a predetermined quantity of heat transfer beads into said tray containing dental instruments or the like;

(d) means incorporated into said tray for selectively releasing said heat transfer beads and retaining said instruments.

13. Apparatus as defined in claim 12 wherein said means for selectively releasing comprises a bottom member for said tray, said bottom member having a plurality of apertures therein, each aperture having a diameter greater than the diameter of said heat transfer beads and means for selectively opening and closing said apertures supported by said instrument tray.

14. Apparatus as defined by claim 13 wherein said means for opening and closing said apertures comprises a planar member generally co-extensive with said bottom member retractably inserted in said tray adjacent said bottom member.

15. Apparatus as defined in claim 12 wherein said means for dispensing comprises a retaining member extending beneath said reservoir and spaced therefrom a predetermined distance said retaining member being selectively movable to an open position and a closed position, said predetermined quantity of beads being a function of the distance between said reservoir and said retaining member.

16. Apparatus as defined in claim 15 wherein said means for heating comprises an open topped column of heat transfer material having an open topped reservoir formed in the upper portion thereof by a transverse partition positioned at a predetermined height therein and selectively movable to an open and a closed position; said column having an opening for inserting said tray at a predetermined height beneath said reservoir and a seat for receiving said tray above said reservoir; and a heater in thermal communication with said column.

17. Apparatus as defined in claim 16 wherein said transverse partition is a planar member retractably inserted transversely within said column.

* * * * *